United States Patent [19]
Hakky et al.

[11] Patent Number: 5,628,727
[45] Date of Patent: May 13, 1997

[54] EXTRACORPOREAL VIRIONCIDAL APPARATUS

[76] Inventors: Said I. Hakky; A-Hamid Hakki, both of 8547 Merrimoor Blvd., E., Largo, Fla. 34647-3145; Perry B. Hudson, 2225 Park St., North, St. Petersburg, Fla. 33710

[21] Appl. No.: 515,135

[22] Filed: Aug. 15, 1995

[51] Int. Cl.⁶ .......................... A61M 37/00; A61M 1/30
[52] U.S. Cl. ...................... 604/6; 604/4; 604/20; 607/154
[58] Field of Search ............... 604/4–6, 20; 210/748, 210/767; 607/154

[56] References Cited

U.S. PATENT DOCUMENTS

| | | | |
|---|---|---|---|
| 4,350,156 | 9/1982 | Malchesky et al. | 604/6 |
| 5,116,307 | 5/1992 | Collins | 604/6 |
| 5,151,192 | 9/1992 | Matkovich et al. | 604/4 |
| 5,188,633 | 2/1993 | Kratzer et al. | 604/5 |
| 5,261,874 | 11/1993 | Castle | 604/4 |
| 5,433,738 | 7/1995 | Stinson | 64/4 |
| 5,484,396 | 1/1996 | Naficy | 604/6 |
| 5,536,238 | 7/1996 | Bischof | 604/6 |

*Primary Examiner*—John G. Weiss
*Assistant Examiner*—Ki Yong O
*Attorney, Agent, or Firm*—John Lezdey

[57] ABSTRACT

An extracorporeal radiation-therapy apparatus for use in treating the blood of a donor for diseased cells or organisms. The apparatus separates the blood by a density gradient device and treats the different blood fractions with drugs and/or high energy radiation.

16 Claims, 4 Drawing Sheets

EXTRACORPOREAL VIRIONCIDAL APPARATUS

BACKGROUND OF THE INVENTION

1. Field of the Invention

This invention relates generally to an apparatus and a method for extracorporeal blood treatment. More particularly, the invention provides an apparatus for treating certain diseases by way of an extracorporeal circuit capable of simultaneously and/or intermittently carrying out three separate modes of treatment.

2. Description of the Prior Art

The exact mode of infection with the Human Immunodeficiency Virus (HIV) is not clear. The commonest method of transmission is contact with body fluid especially blood products. The clinical stages of HIV infection can be divided into the exposure phase, acute phase, asymptomatic phase, and finally the Acquired Immune Deficiency Syndrome (AIDS) phase. In the acute stage (after exposure), the patient develops symptoms suggestive of influenza, i.e., congested nasal sinuses, headaches, generalized muscle pain, back pain, and low grade fever. These symptoms last for a few days or weeks. During this phase the blood will contain a high concentration of HIV viruses. In the asymptomatic phase, the patient will have no symptoms, however the macrophages, lyphocytes as well as the glial cells are attacked continuously by HIV viruses. This phase may last for months or years. The final stage is AIDS, where the patient loses his immune system and becomes susceptible to intractable infections that will eventually terminate his life.

HIV virus consists of double strand of ribonucleic acid together with a DNA polymerase enzyme called reverse transcriptase which transcribes single stranded viral RNA into numerous copies of double stranded DNA when entering the susceptible cell. The viral DNA enters the host cell nucleus and some of which will be integrated into the cell chromosomal DNA. This is called a provirus. This coincides with the acute phase of infection. This HIV pro-viral transcription can also be switched by other viruses such as Herpes Simplex Type I, Cytomegalovirus, Varicella Zoster Virus, and Hepatitis Virus. When the proper signals are received by the viral DNA, copies of the viral RNA proceeds. In the cytoplasm, the viral mRNA (messenger RNA) are translated into viral protein. A new virion will bud from the cell surface together with a piece of plasma membrane forming the envelop of the virus. Millions of virion are manipulated by the HIV and leads to a complete collapse of the immune system. This is the stage that the patient has the Acquired Immune Deficiency Syndrome, i.e., AIDS. The patients become susceptible to minor infection which will bring their demise.

Prior art devices are known for carrying out extracorporeal treatment of the blood. Many extracorporeal treatment methods have become well established as routine methods of treating specific conditions or diseases. Examples of extracorporeal treatment methods of known effectiveness include those adapted for extracorporeal blood oxygenation, plasmapheresis, radiotherapy, and extracorporeal treatment by pharmacological and chemotherapeutic agents.

Specific examples of extracorporeal blood treatment devices and methods are described in the following:

U.S. Pat. No. 4,692,138 issued to Troutnet, et al. discloses a pump block which is used to interface an irradiation chamber with a roller pump. Such a pump block is incorporated into an extracorporeal apparatus wherein photoactivatable agents are added to the patient's blood prior to extracorporeal irradiation of the blood. After such irradiation is completed, the blood is returned to the patient.

U.S. Pat. No. 4,321,918 to Clark, discloses a process and method of extracorporeal irradiating whole blood to alter lymphocyte function.

U.S. Pat. No. 4,576,143 issued to Clark discloses a process and method of extracorporeal irradiating whole blood for the purpose of modifying the immune response in humans affected with immune disorders.

U.S. Pat. No. 4,683,689 to Edelson teaches a method and system for externally treating the blood of a cancer patient with UV radiation for reducing undesirable cell population. A photoactive chemical agent having an affinity for nucleic acid cells intermolecular attractive forces draw the agent into an intercalated relationship with the nucleic acids of the lymphocytes. Prior to activation, the agent has little or no effect on the cell chemistry. However, upon irradiation the agent forms certain covalent attachments or otherwise complexes with nucleic acids of the cell. Thereby inactivating the nucleic acid chains and inhibiting the metabolic functions of the cell. In this manner, the cell's processes, having been disrupted, and in particular its ability to divide prevented, inactivation or death of the cell results.

None of these extracorporeal irradiation methods and devices of the prior art have been specifically designed for the treatment of blood infected with HIV. The T-lymphocytes which contain or have been infected by the HIV virus may become structurally fragile. This suggests that such cells may be selectively disrupted or destroyed. Furthermore, these extracorporeal blood treatments are conducted on whole blood, none of the references disclose, teach, or suggest, separating whole blood into its components and separately treating each blood component under the most effective treatment conditions, reconstituting the blood component and returning the reconstituted blood to the patient.

U.S. Pat. Nos. 5,074,838 and 5,104,373 relate the extracorporeal devices for the treatment of blood infected with the HIV virus at elevated blood temperatures.

U.S. Pat. No. 5,074,838 to Kroyer describes an extracorporeal thermo-therapy device to raise the blood temperature around two degrees centigrade above normal body temperatures to destroy or attenuate HIV viruses and cancer cells.

U.S. Pat. No. 5,104,373 to Davidner et al., discloses an extracorporeal apparatus and method for treating certain blood borne infections including infections with HIV virus by three treatment modalities which can be conducted simultaneously or separately. The first modality comprises a means for hyperthermically treating the blood at a reduced pH under variable flow conditions. The second modality involves a means for mechanically shearing blood cells which disrupts the infected cells and/or separates viral particles from the host cells or potential host cells. The third modality involves means for subjecting whole blood or the mononuclear leukocyte component to irradiation frequencies selected from X-ray, ultraviolet, infrared, visible, laser or radio frequencies prior to recombing the treated cells with the remaining blood plasma and/or other formed elements.

The apparatus and method of the present invention differs from the apparatus and methods referred to above in the prior art patents. This difference provides for a treatment of viruses and other unwanted cells by fractionating the blood into components which can be separately treated with high energy electromagnetic radiation allowing for optimum processing conditions for each fraction.

SUMMARY OF THE INVENTION

In accordance with the present invention an apparatus and method for extracorporeally treating blood by radiation therapy is provided. Such treatment allows for more control of the amount of radiation impinged upon each blood fraction. Therefore, this invention provides a more effective device and method in inactivating diseased cells or organisms capable of division without harmful effects to the reconstituted blood.

In accordance with one aspect of the invention there is provided an extracorporeal blood treatment device for use in treating the blood of a donor for diseased cells or organisms capable of division comprising:

A. means for removing a flow of blood from donor;
B. a housing comprising;
   a first fluid communication means for receiving said blood and subjecting said blood to a density gradient device whereby blood fractions selected from plasma, white blood cells and platelets are separated;
   a second, third and fourth fluid condition means for transferring each separated blood fraction to individual treatment chambers;
   each treatment chamber having side walls impenetrable to high energy electromagnetic radiation source and is equipped with at least one module having side walls substantially transparent to said radiation and containing a semi-permeable membrane and a high energy thermomagnetic source;
   said module includes a fifth fluid communication means to supply a continuous flow of a complexing agent into said module; and a sixth fluid communication means to remove the complexing agent effluent;
   the high energy electromagnetic radiation source being of an effective wavelength and intensity to inactive said diseased cells or organisms capable of division and being directed to impinge upon said modules to provide an irradiated filtrate;
   a third fluid communication means for receiving said irradiated filtrate substantially free of diseased cells from each fraction to produce reconstituted blood; and
C. connector means adapted to return said reconstituted blood to the donor.

A principle object of the invention is to provide an extracorporeal-radiation device for treating blood containing pathogenic cells or organisms capable of division, e.g., lymphocytes, protozoans, bacteria, and viruses including the HIV virus.

Another object of the invention is to provide a novel method of treating HIV cells attached to macrophages or HIV cells contained in the blood stream.

A further object of the invention is to provide an apparatus wherein separation means and the radiation source are combined under the same housing.

Yet another object of the invention is to provide an effective continuous blood sterilization extracorporeal-radiation method.

Still another object of the present invention is to provide an extracorporeal radiation device in which a bundle of the filtering hollow fibers, are preassembled in the form of a module can be exchanged and replaced rapidly.

DETAILED DESCRIPTION OF THE PREFERRED EMBODIMENTS

Figure 1:
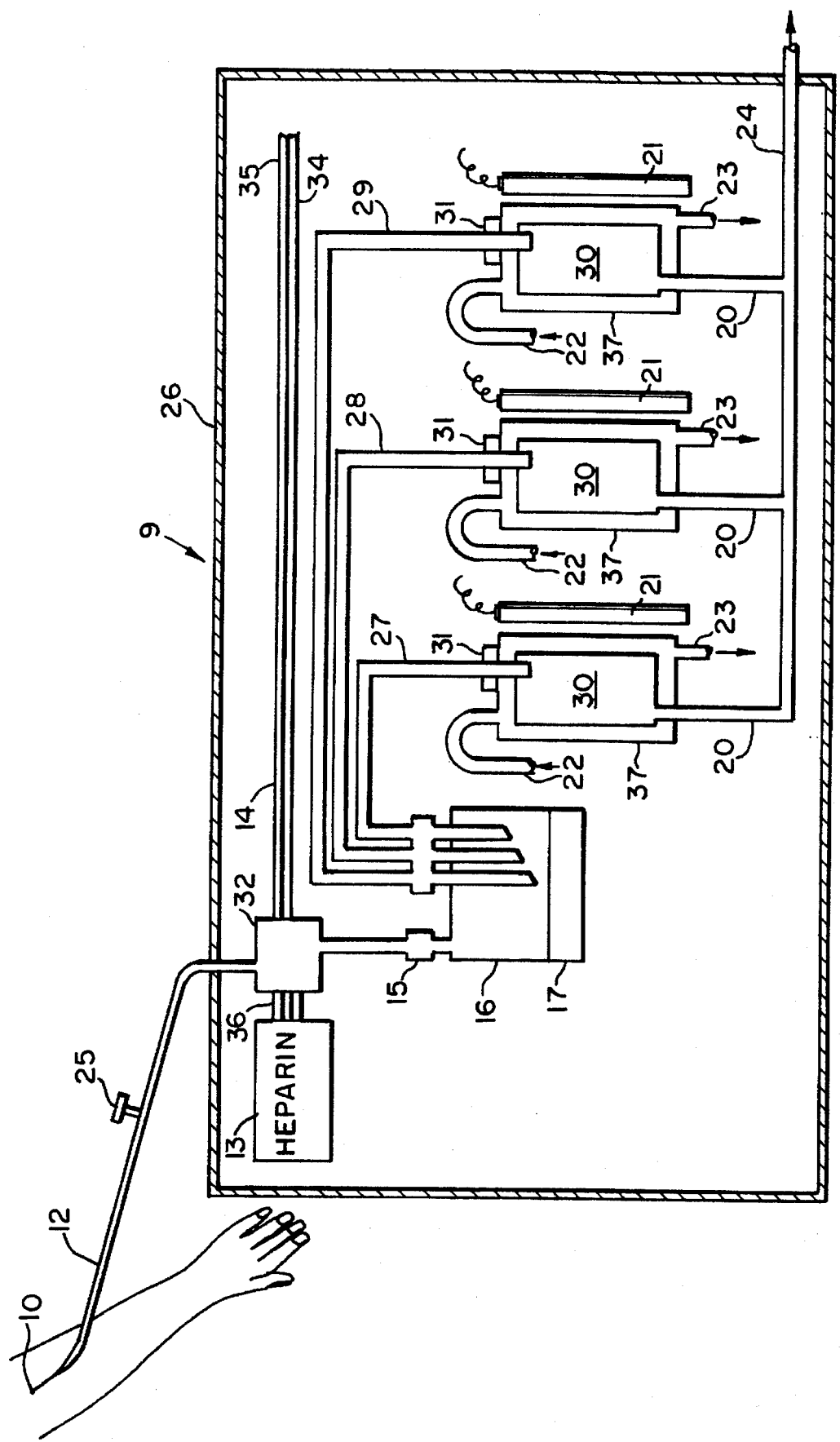
FIG. 1 shows a side elevational view of the extracorporeal-radiation therapy apparatus of this invention including the separation means and radiation source in a single housing including a system for removing a flow of blood from a donor.

Referring now to the drawing wherein the illustrations are for the purpose of showing preferred embodiments of the apparatus according to the present invention and not for the purpose of limiting its scope.

FIG. 1 shows a preferred embodiment of the extracorporeal apparatus 9 according to the present invention. As with any extracorporeal apparatus, the initial step is to withdraw blood from a donor. Such withdrawal of blood is generally accomplished by insertion of an exit needle 10 into a sizeable vein such as the femoral vein. A re-entry needle (not shown) is generally connected to another part of the body such as the other arm. A conventional hypodermic needle or catheter about size 18–20 gauge may be used.

In the apparatus 9 according to the present invention, the exit needle 10 will transmit the blood flow from the donor through a clear plastic tube 12 such as a Silastic tube equipped with regulator 15. Preferably, an anticoagulant such as heparin is mixed with the withdrawn blood. Reservoir 13 supplies heparin through tube 36 to the withdrawn blood by regulator 32. As better shown in FIG. 2, the withdrawn blood is mixed with heparin before it is added to centrifuge 17. The amount of heparin added is about 1000 units per liter of blood. The mixed blood is directed via line 33 to pump 15 to be charged into a first centrifuge 17. Regulator 32 delivers the withdrawn blood at a rate of 40 milliliters per minute to first centrifuge device 17 containing a flexible plastic bag 16. This bag can also be of Silastic material. When the first centrifuge 17 is filled, valve 15 prevents further addition of blood. Then regulator 32 directs blood through tube 34, and heparin through tube 35 to a second centrifuge (not shown) via tubing (not shown). Likewise, when the second centrifuge is filled, the regulator 32 will direct blood to a third centrifuge (not shown). Each centrifuge operates as an independent unit.

Figure 2:
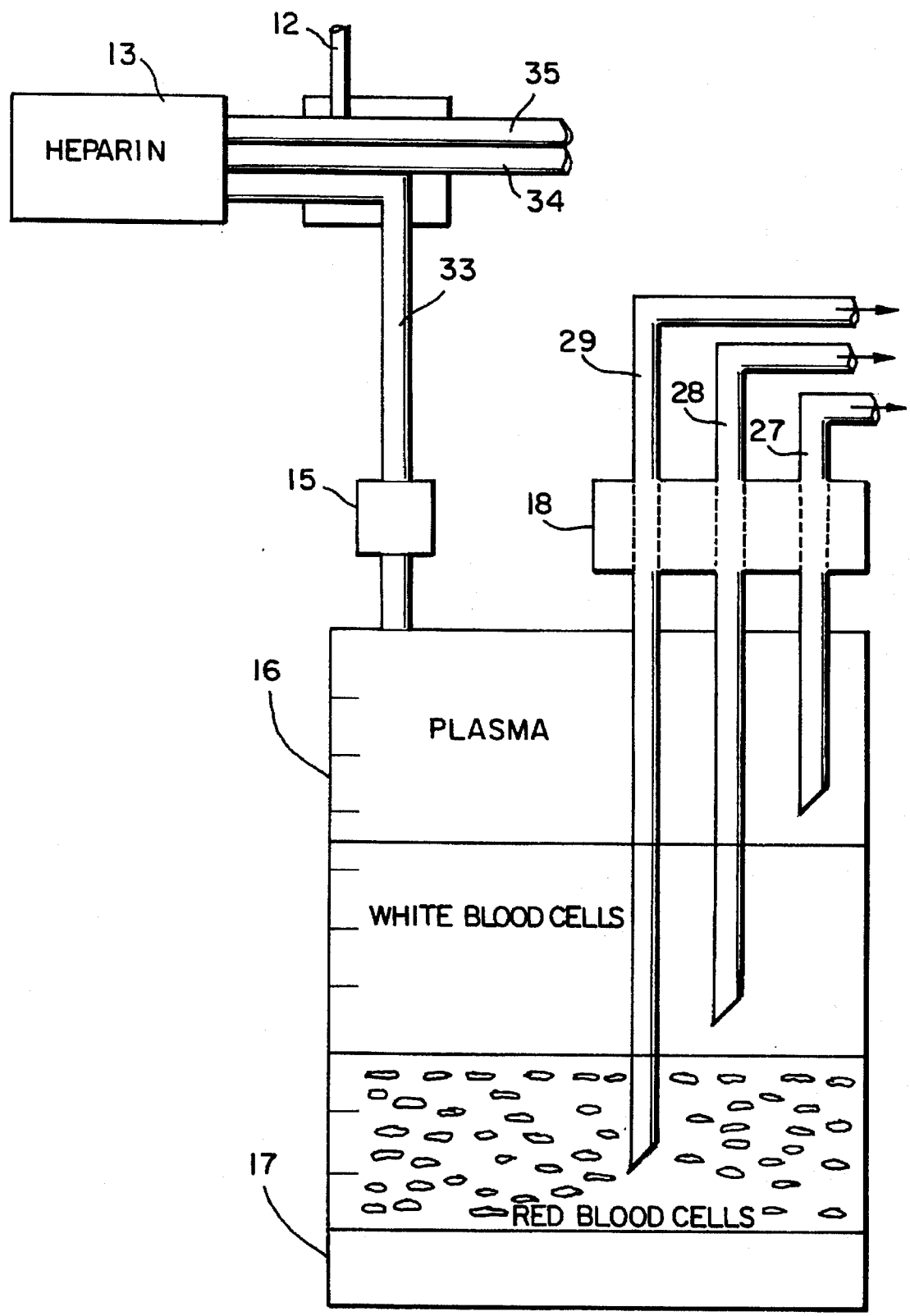
FIG. 2 illustrates a side elevational enlarged view of the density gradient device of this invention comprising a graduate vessel, blood fractions, and a centrifuge.

FIG. 2 shows centrifuge 17 which is representative of the other centrifuges used in the system. Each contains a graduated flexible plastic bag. Besides the inlet tube 33 each flexible plastic bag contains three exit tubes to carry the three major fractions of blood components. Centrifuge 17 is operated at about 500 r.p.m. for about five minutes to produce three layers, i.e., plasma, white blood cells/platelets and red blood cells.

Figure 3:
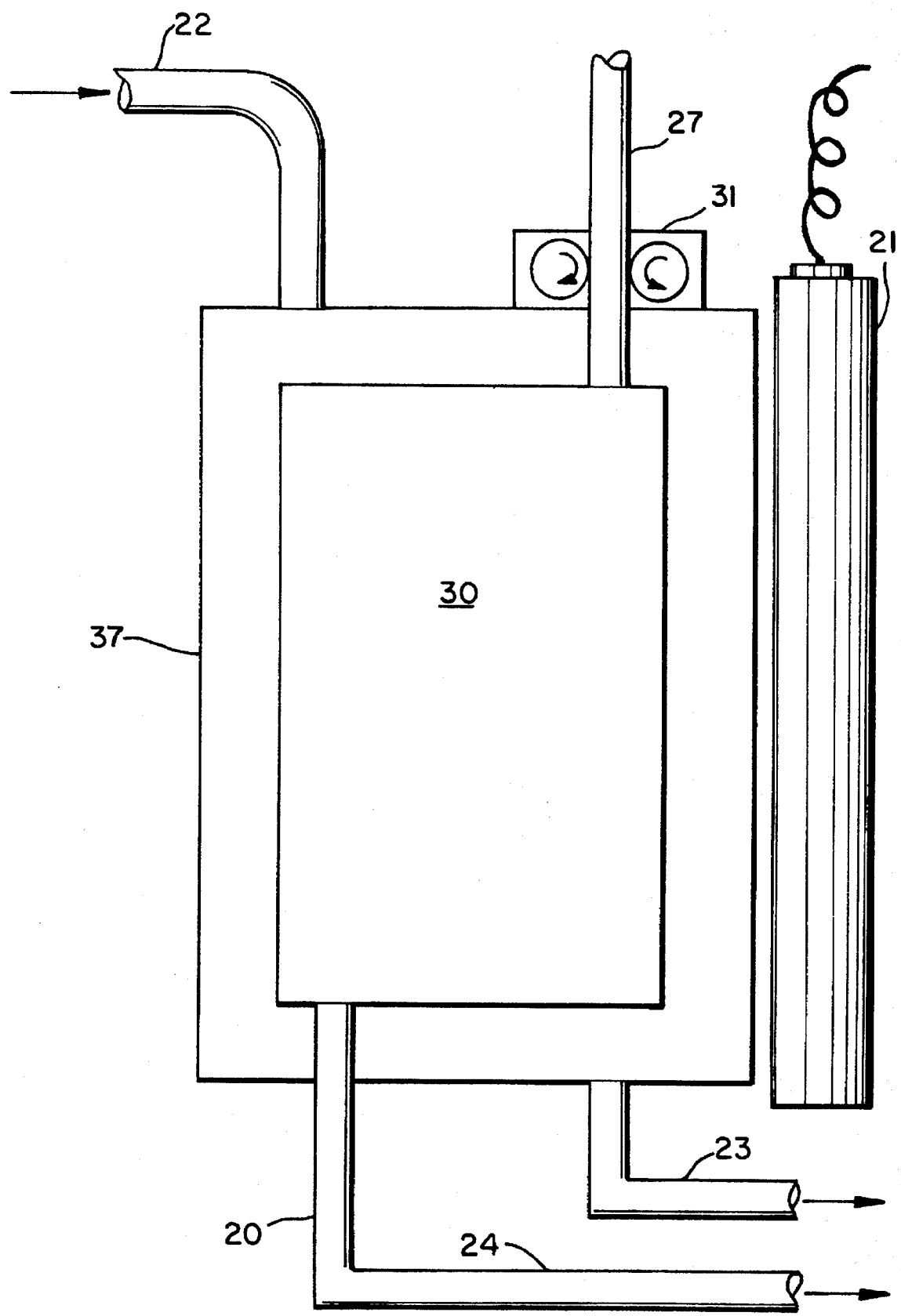
FIG. 3 shows a side elevational view of a separate radiation treatment chamber of this invention which comprises an outer housing, a semi-permeable membrane module having inlet and outlet parts and a radiation source.

FIG. 3 shows a typical radiation treatment chamber 37 of the invention as illustrated in FIG. 1. The radiation treatment chamber 37 may be made of thermoplastic polymers, thermoset polymers, metals or ceramic materials with the provision that the side walls separating each compartment are impenetrable to high energy electromagnetic radiation, comprising a blood fraction inlet tube 27, inlet pump 31, module 30, complexing agent inlet line 22, complexing agent outlet line 23, and a high energy electromagnetic radiation source.

Figure 4:
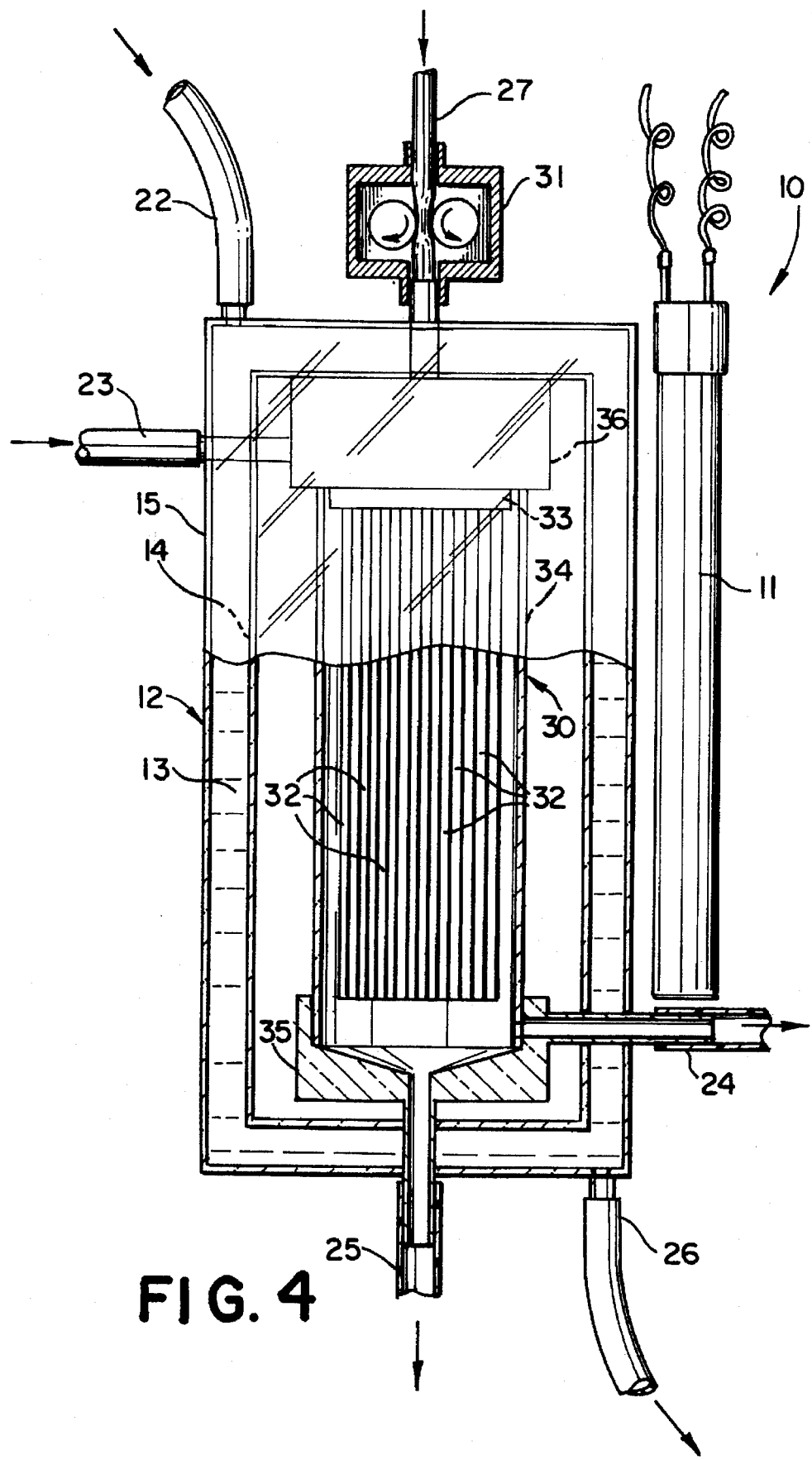
FIG. 4 is a sectional view of the semi-permeable module having the upper portion of a bundle of hollow fibers supported by a tubular cap member.

Referring now to FIG. 4, a filtration component using hollow fibers membrane is shown as module 30 and includes a housing 41 in which a bundle of hollow fibers 43, and the conical cap member 44 is fixed to collecting and fixing component 45. A cover member 42 mounted on the opening of housing 41 in a liquid tight manner is provided with an opening communicating with an inlet for the blood fraction 53 at the center of cover member 42. On the upper side wall of cover member 42, an inlet 50 for the complexing agent is provided. The protruding portion 49 of conical member 44 is connected with the collecting and fixing position portion 45, and is inserted into an opening communicating with blood fraction 53 with the joint sealed by two O rings 45. A band 57 coupling housing 41 with cover member 42 in a liquid-tight manner with seal 58. O ring 55, seal 58 and complexing agent chamber 59 and blood fraction chamber form a liquid tight structure with a membrane of hollow fibers 43 between the complexing agent chamber 59 and blood fraction chamber 60. A similar filtration component in U.S. Pat. No. 4,547,289 to Okam, et. al., and is incorporated by reference herein.

Referring to FIGS. 1–4, in the case of a blood fraction infected with the HIV virus, the blood fraction supplied by centrifuge 16 through line 27 is moved by pump 31 to inlet 53 of module 30 and is directed to the inside of the hollow fibers 43. The HIV virus has a size about 100 nanometers (nm). Therefore, it is necessary that the average pore diameter and the maximum pore diameter of the porous polymeric hollow fibers of the module 30 fall within respective ranges which are predetermined in accordance with the size of the virus, which is to be transferred through the membrane. The hollow fibers are designed so the HIV virus can permeate through them while the blood fraction are held inside the tubacles and exit through outlet 51 to tube 20 which is in combination with recombing tube 24. At the same time, a complexing agent is introduced into module 30 via tube 22 through inlet 50 around chamber 59 to contact the bundle of hollow fibers 53. The complexing agent for HIV viruses is preferably a sulfonated polysaccharide.

Most preferably, a sulfonated polysaccharide such as a dextran sulfate having a molecular weight of about 5000–8000 is slowly and continuously introduced to contact the HIV viruses. A solution of dextran sulfate at a concentration of 1–6 gm/ml having an average molecular weight would be suitable for the purposes of this invention. This solution attracts the HIV virus and is virioncidal without any harmful effect on the different blood components.

The continuous flow of the dextran sulfate solution, the thinness of the hollow fibers and the slow blood flow allows almost every cell to be exposed to the virioncidal effect. The effect extends into the hollow tubes which contain blood fractions, e.g., plasma, white blood cells/platelets and red blood cells.

A high energy electromagnetic radiation source is positioned to emit radiation into the bundle of hollow fibers 53 to irradiate the blood fractions passing through the hollow fibers, as well as, the HIV viruses held in the dextran solution in the chamber 59.

The high energy electromagnetic radiation source may be selected from x-ray, ultraviolet, infra-red, and laser energy. Helium-neon and Helium-cadmium laser irradiation, at certain wavelengths have certain immunostimulative and immunosuppressive effects on blood constituents in vitro. Ultraviolet radiation known to be effective in inactivating microorganisms may be used in the apparatus and method according to this invention. Suitable ultraviolet radiation sources include those producing radiation in the wavelength range from 100 to nm preferably from 200 to 350 nm for example UV-A at approximately 320 to 400 nm, UV-B at approximately 254 nm. Advantageously, the ultraviolet source are lamps which are connected to a timer and a control unit (not shown) for controlling the duration of the irradiation. As suitable ultraviolet source is in the form of a plurality of eight tubes disposed generally parallel to and around the module 30. Module 30 is constructed of, preferably, a plastic substantially transparent to a high energy electromagnetic radiation source such as polyurethane. Other transparent materials which would be useful include: polytetrafluoroethylene, low density polyethylene, polyvinyl chloride, and ceramics. Preferably, module 30 is a clear plastic tube which contains a plurality of micro tubules. Each micro tubules is a hollow fiber about 20–30 microns in diameter and about 20 centimeters long. Module 30 contains 20,000 to 30,000 micro tubules. Thus, the plurality of hollow cores of the multiplicity of fibers within each module define numerous passageways in fluid communication with the blood fraction outlet tube 20. Further, a complexing agent such as a low molecular weight dextran, specifically dextran sulfate is slowly and continuously flowed through and around the semi-permeable membranes.

The selective permeability of the micro tubules slows the transfer of material through the membrane and enables longer contact of the complexing agent with the pathogen with increased complex formation. This increased formation of the pathogen-agent complex coupled with the thinness of these micro tubules and the slow rate of flow affords a much more effective radiation treatment. Such treatment conditions are maintained for approximately 2 to 20 minutes.

Furthermore, as pointed out above the radiation dosage can be tailored according to the content of the treatment compartment and the genotype of the HIV virus. For example, the plasma fraction can receive a higher dose of radiation than the white blood cells/platelets. The red blood cells can receive a higher dose than the white cells and less dosage than the plasma. Thus, different blood components will be irradiated differently to ensure sterilization of the blood without harming the patient's blood. This is the unique feature of this invention, i.e., the radiation dosage in each chamber can be very carefully controlled to eliminate damage to the blood fraction. From tube 24 blood will be sampled to test for the presence of HIV virus by the standard available test. Also, blood samples are taken to check the level of mineral and electrolyte content, thus ensuring a safer sterile blood returned back to the patient.

What is claimed is:

1. An extracorporeal radiation-therapy apparatus for use in treating the blood of a donor for diseased cells or organisms capable of division comprising:

a. means for removing a flow of blood from donor;

b. a housing comprising;

a first fluid communication means for receiving said blood and subjecting said blood to a density gradient device whereby blood fractions selected from plasma, white blood cells and platelets are separated;

a second, third and fourth fluid condition means for transferring each separated blood fraction to individual treatment chambers;

each said treatment chambers having side walls impenetrable to high energy electromagnetic radiation so as to inactivate said diseased cells or organisms, a high energy electromagnetic radiation source and at least one module treating chamber having side walls substantially transparent to said radiation and containing a semi-permeable membrane;

said at least one module includes a fifth fluid communication means to supply a continuous flow of a complexing agent for viral particles into said module and returning said unreacted complexing agent to a complexing agent reservoir;

said high energy electromagnetic radiation source being of an effective wavelength and intensity to inactive said diseased cells or organisms capable of division and being directed to impinge upon said at least one module to provide an irradiated filtrate;

a third fluid communication means for receiving said irradiated filtrate substantially free of diseased cells from each of said modules and combining the irradiated filtrates of each fraction to produce recombined blood; and c. means for returning said recombined blood to the donor.

2. The apparatus of claim 1 wherein said density gradient device comprises a centrifuge.

3. The apparatus of claim 2 wherein said density gradient device comprises a plurality of centrifuges.

4. The apparatus of claim 3 wherein said plurality of centrifuges are connected in series.

5. The apparatus of claim 1 wherein said first fluid communication means includes an anticoagulant reservoir means for introducing an anticoagulant into the removed blood prior to charging said gradient device.

6. The apparatus of claim 5 wherein the anticoagulant is heparin.

7. The apparatus of claim 1 wherein said at least one module are made of clear plastic.

8. The apparatus of claim 7 wherein said clear plastic is polystyrene or polyurethane.

9. The apparatus of claim 1 wherein said at least one module contain a plurality of microtubules.

10. The apparatus of claim 1 wherein the complexing agent in said second, third and fourth fluid communication is dextran sulfate.

11. The apparatus of claim 1 wherein the high energy electromagnetic radiation source is selected from X-ray, ultraviolet, infra-red, laser and radio frequency.

12. The apparatus of claim 11 wherein said radiation source is infra-red.

13. The apparatus of claim 11 wherein said radiation source is ultraviolet.

14. The apparatus of claim 1 including a pump means located at an inlet of each said treatment chamber.

15. The apparatus of claim 14 wherein said pump means comprises two rotating cylinders.

16. The apparatus of claim 1 wherein said effective wavelength and intensity varies in each treatment chamber.

* * * * *